US 7,655,799 B2

(12) United States Patent
Ma et al.

(10) Patent No.: US 7,655,799 B2
(45) Date of Patent: *Feb. 2, 2010

(54) 2{[2-(SUBSTITUTED AMINO)ETHYL]SULFONYL}ETHYL N,N,N',N'-TETRAKIS(2-CHLOROETHYL) PHOSPHORODIAMIDATES

(75) Inventors: Wenli Ma, Union City, CA (US); Kevin T. Weber, Carmel, IN (US); Robert M. Yee, San Francisco, CA (US)

(73) Assignee: Telik, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/564,744

(22) Filed: Nov. 29, 2006

(65) Prior Publication Data

US 2008/0125398 A1    May 29, 2008

(51) Int. Cl.
*A61K 31/435* (2006.01)
*C07F 9/572* (2006.01)
*C07F 9/576* (2006.01)

(52) U.S. Cl. .................. 546/22; 548/413; 514/277; 514/76

(58) Field of Classification Search ............... 514/277, 514/76; 546/22; 548/413
See application file for complete search history.

(56) References Cited

U.S. PATENT DOCUMENTS 5,556,942 A    9/1996    Kauvar et al.

6,506,739 B1    1/2003    Herr et al.
2005/0267075 A1    12/2005    Allen et al.

FOREIGN PATENT DOCUMENTS

| WO | WO 95/09866 A1 | 4/1995 |
| WO | WO 01/83496 A1 | 11/2001 |
| WO | WO 2005/118601 A2 | 12/2005 |

OTHER PUBLICATIONS

U.S. Appl. No. 60/588,436, filed Dec. 1, 2005, Allen et al.
Morgan AS et al., "Tumor Efficacy and Bone Marrow-sparing Properties of TER286, a Cytotoxin Activated by Glutathione S-Transferase", *Cancer Res.*, v.58, pp. 2568-2575, Jun. 15, 1998.
Rosario LA, et al., "Cellular Response to a Glutathione S-Transferase P1-1 Activated Prodrug", *Mol. Pharmacol.*, v. 58, pp. 167-174, Jul. 2000.
Jain M et al., "Sulfonyl-containing aldophosphamide analogues as novel anticancer prodrugs targeted against cyclophosphamide-resistant tumor cell lines", *J. Med. Chem.*, v.47, pp. 3843-3852, Jul. 15, 2004 (published on Web Jun. 17, 2004).
TEW K.D. "TLK-286: A novel glutathione S-transferase-activated prodrug". Expert Opinion on Investigational Drugs, Ashley Publications Ltd., London, GB, vol. 14, No. 8, 2005, pp. 1047-1054.

*Primary Examiner*—Rita J Desai
(74) *Attorney, Agent, or Firm*—Swiss Tanner, P.C.

(57) ABSTRACT

2-{[2-(Substituted amino)ethyl]sulfonyl}ethyl N,N,N',N'-tetrakis(2-chloroethyl)-phosphorodiamidates, their preparation and intermediates in their preparation, pharmaceutical compositions containing them, and methods of treatment using them. The compounds are useful for treating cancer, alone and in combination with other anticancer therapies.

18 Claims, No Drawings

2{[2-(SUBSTITUTED AMINO)ETHYL]SULFONYL}ETHYL N,N,N',N'-TETRAKIS(2-CHLOROETHYL) PHOSPHORODIAMIDATES

BACKGROUND OF THE INVENTION

1. Field of the Invention

This invention relates to 2-{[2-(substituted amino)ethyl]sulfonyl}ethyl N,N,N',N'-tetrakis(2-chloroethyl)phosphorodiamidates, pharmaceutical compositions containing them, their pharmaceutical use, and their preparation and intermediates in their preparation.

2. Description of the Related Art

U.S. Pat. No. 5,556,942 [and PCT Publication No. WO 95/09865] discloses compounds of the formula

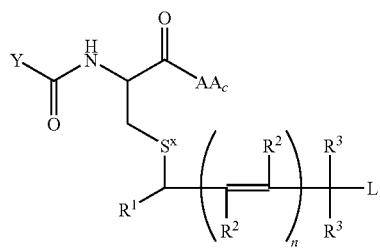

and their amides, esters, and salts, where:

L is an electron withdrawing leaving group;

$S^X$ is —S(=O)—, —S(=O)$_2$—, —S(=NH)—, —S(=O)(=NH)—, —S$^+$(C$_1$-C$_6$ alkyl)-, —Se(=O)—, —Se(=O)$_2$—, —Se(=NH)—, or —Se(=O)(=NH)—, or is —O—C(=O)—, or —HN—C(=O)—;

each $R^1$, $R^2$ and $R^3$ is independently H or a non-interfering substituent;

n is 0, 1 or 2;

Y is selected from the group consisting of

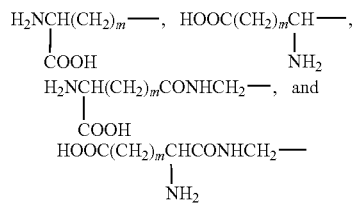

where m is 1 or 2; and $AA_c$ is an amino acid linked through a peptide bond to the remainder of the compound.

The compounds are stated to be useful drugs for the selective treatment of target tissues which contain compatible glutathione S-transferase (GST) isoenzymes, and simultaneously elevate the levels of granulocyte macrophage progenitor cells in bone marrow. Disclosed embodiments for L include those that generate a drug that is cytotoxic to unwanted cells, including the phosphoramidate and phosphorodiamidate mustards.

One of the compounds has the formula

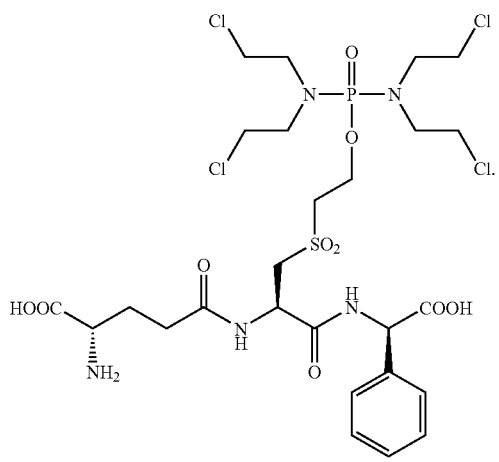

It is referred to in the patent as TER 286 and named as γ-glutamyl-α-amino-β-((2-ethyl-N,N,N,N-tetra(2'-chloro)ethylphosphoramidate)sulfonyl)propionyl-(R)-(−)-phenylglycine. This compound, later referred to as TLK286, has the uninverted CAS name L-γ-glutamyl-3-[[2-[[bis[bis(2-chloroethyl)amino]phosphinyl]oxy]ethyl]sulfonyl]-L-alanyl-2-phenyl-(2R)-glycine. As the neutral compound, its recommended International Nonproprietary Name is canfosfamide; and as its hydrochloride acid addition salt, its United States Adopted Name is canfosfamide hydrochloride. Canfosfamide and its salts are anticancer compounds that are activated by the actions of GST P1-1, and by GST A1-1, to release the cytotoxic phosphorodiamidate mustard moiety.

In vitro, canfosfamide has been shown to be more potent in the M6709 human colon carcinoma cell line selected for resistance to doxorubicin and the MCF-7 human breast carcinoma cell line selected for resistance to cyclophosphamide, both of which overexpress GST P1-1, over their parental cell lines; and in murine xenografts of M7609 engineered to have high, medium, and low levels of GST P1-1, the potency of canfosfamide hydrochloride was positively correlated with the level of GST P1-1 (Morgan et al., "Tumor efficacy and bone marrow-sparing properties of TER286, a cytotoxin activated by glutathione S-transferase", *Cancer Res.*, 58, 2568-2575 (1998)).

Canfosfamide hydrochloride is currently being evaluated in multiple clinical trials for the treatment of ovarian, breast, non-small cell lung, and colorectal cancers. It has demonstrated significant single agent antitumor activity and improvement in survival in patients with non-small cell lung cancer and ovarian cancer, and single agent antitumor activity in colorectal and breast cancer. Evidence from in vitro cell culture and tumor biopsies indicates that canfosfamide is non-cross-resistant to platinum, paclitaxel, and doxorubicin (Rosario et al., "Cellular response to a glutathione S-transferase P1-1 activated prodrug", *Mol. Pharmacol.*, 58, 167-174 (2000)), and also to gemcitabine. Patients treated with canfosfamide hydrochloride show a very low incidence of clinically significant hematological toxicity.

PCT Publication No. WO 95/09865 also discloses intermediates that are compounds of the formula

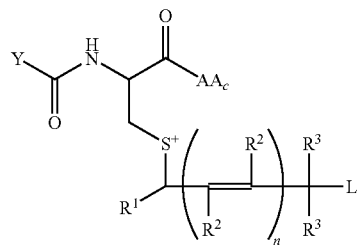

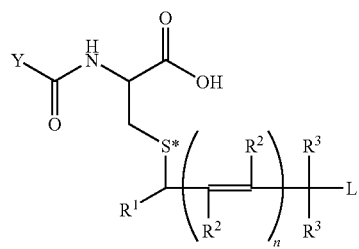

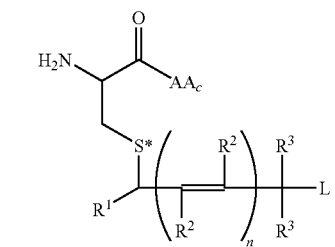

and their amides, esters, and salts, where:

L is an electron withdrawing leaving group;

S⁺ is S or Se;

S* is —S(=O)—, —S(=O)₂—, —S(=NH)—, —S(=O)(=NH)—, —S⁺(C₁-C₆ alkyl)-, —Se(=O)—, —Se(=O)₂—, —Se(=NH)—, or —Se(=O)(=NH)—, or is —O—C(=O)—, or —HN—C(=O)—;

each R¹, R² and R³ is independently H or a non-interfering substituent;

n is 0, 1 or 2;

Y is selected from the group consisting of

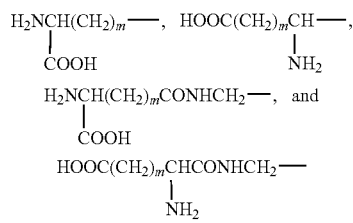

where m is 1 or 2; and

AA_c is an amino acid linked through a peptide bond to the remainder of the compound.

U.S. Pat. No. 6,506,739 discloses compounds of the formula

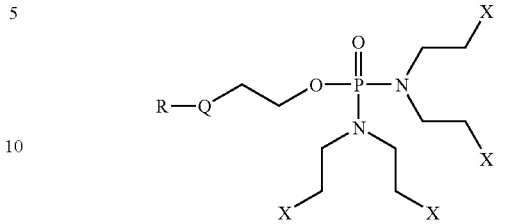

where:

X is a halogen atom;

Q is O, S, or NH; and R is hydrogen, optionally substituted lower alkyl, optionally substituted aryl, or optionally substituted heteroaryl, or is R'CO—, R'NHCO—, R'SO₂—, or R'NHSO₂— where R' is hydrogen, optionally substituted lower alkyl, optionally substituted aryl, or optionally substituted heteroaryl; or R-Q together is chlorine;

and their salts, as antitumor agents.

US Patent Application Publication No. 2005/0267075 [and PCT Publication No. WO 2005/118601] discloses compounds of the formulae

A

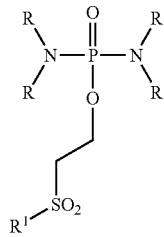

B

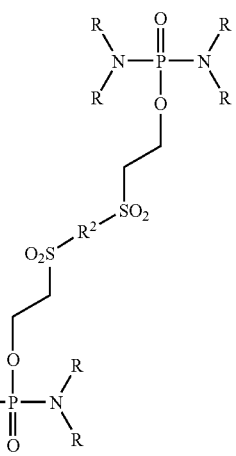

-continued

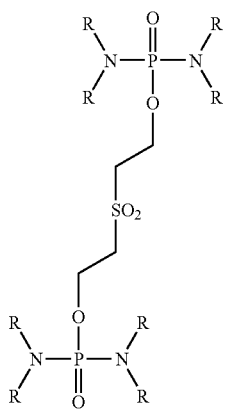

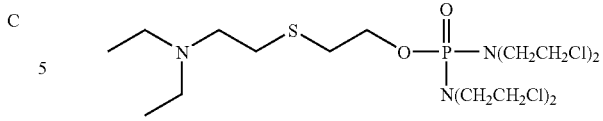

as compounds 13AA and 14AA on page 26.

Jain et al., "Sulfonyl-containing aldophosphamide analogues as novel anticancer prodrugs targeted against cyclophosphamide-resistant tumor cell lines", *J. Med. Chem.*, 47(15), 3843-3852 (2004), discloses a series of sulfonylethyl phosphorodiamidates of the formula

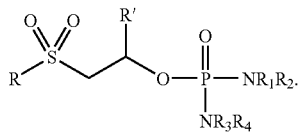

where:

each R is independently hydrogen, $C_{1-6}$ alkyl, or —$CH_2CH_2X$, where each X is independently Cl, Br, $C_{1-6}$ alkanesulfonyloxy, halo-$C_{1-6}$ alkanesulfonyloxy, or benzenesulfonyloxy optionally substituted with up to three substituents selected from halo, $C_{1-3}$ alkyl, halo-$C_{1-3}$ alkyl, $C_{1-3}$ alkyloxy, or halo-$C_{1-3}$ alkyloxy, provided that at least two R's in each phosphorodiamidate group are —$CH_2CH_2X$;

$R^1$ is optionally substituted alkyl, optionally substituted heteroalkyl, optionally substituted aryl, optionally substituted aralkyl, optionally substituted heteroaryl, or optionally substituted heteroaralkyl; and $R^2$ is optionally substituted alkanediyl, optionally substituted heteroalkanediyl, optionally substituted arenediyl, optionally substituted arenedialkyl, optionally substituted heteroarenediyl, or optionally substituted heteroarenedialkyl, and their salts, as antitumor agents.

The compound of the formula

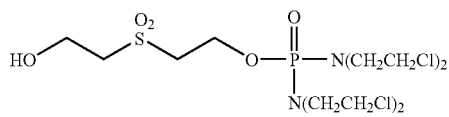

is disclosed as compound 16A on page 19 of US Patent Application Publication No. 2005/0267075.

U.S. Patent Application No. 60/588,436, laid open with the publication of US Patent Application Publication No. 2005/0267075 and PCT Publication No. WO 2005/118601, discloses the compounds of the formulae

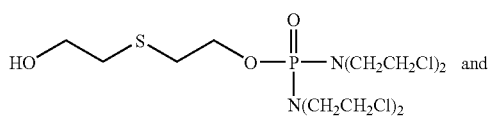

The compounds are said to spontaneously liberate phosphoramide mustards via beta-elimination, and to be more potent than the corresponding phosphoramide mustards against V-79 Chinese hamster lung fibroblasts in vitro. Some of the compounds were said to show excellent in vivo antitumor activity in CD2F1 mice against the P388/0 (wild) and P388/CPA (cyclophosphamide-resistant) leukemia cell lines.

It would be desirable to develop chemically and pharmaceutically simple (easy to synthesize and formulate) anticancer drugs having an efficacy and safety as good or better than canfosfamide.

The disclosures of the documents referred to in this application are incorporated into this application by reference.

SUMMARY OF THE INVENTION

In a first aspect, this invention is compounds of formula A:

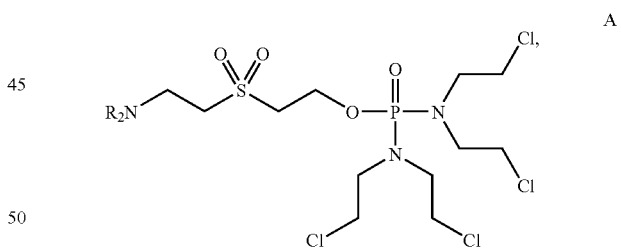

and their acid addition salts, where each R is independently methyl, ethyl, propyl, or isopropyl, or —$NR_2$ together is 1-pyrrolidinyl or 1-piperidinyl.

In a second aspect, this invention is pharmaceutical compositions comprising a compound of the first aspect of this invention.

In a third aspect, this invention is methods of treating cancer by the administration of a compound of the first aspect of this invention or a pharmaceutical composition of the second aspect of this invention; alone or in combination with other anticancer therapies.

In a fourth aspect, this invention is methods of preparing compounds of the first aspect of this invention, and intermediates in the methods.

DETAILED DESCRIPTION OF THE INVENTION

Definitions

"Acid addition salts" are described in the section entitled "Compounds of this invention".

A "therapeutically effective amount" means that amount which, when administered to a human for treating a cancer, is sufficient to effect treatment for the cancer. "Treating" or "treatment" of a cancer in a human includes one or more of:

(1) limiting/inhibiting growth of the cancer, i.e., limiting/arresting its development, (2) reducing/preventing spread of the cancer, i.e. reducing/preventing metastases, (3) relieving the cancer, i.e., causing regression of the cancer, (4) reducing/preventing recurrence of the cancer, and (5) palliating symptoms of the cancer.

"Combination therapy" means the administration of a compound of the first aspects of this invention and another anticancer therapy during the course of cancer chemotherapy. Such combination therapy may involve the administration of the compound of the first aspect of this invention before, during, and/or after the administration of the another anticancer therapy. The administration of the compound of the first aspect of this invention may be separated in time from the administration of the another anticancer therapy by up to several weeks, and may precede it or follow it, but more commonly the administration of the compound of the first aspect of this invention will accompany at least one aspect of the another anticancer therapy (such as the administration of one dose of a chemotherapeutic agent, molecular targeted therapy agent, biologic therapy agent, or radiation therapy) within up to 48 hours, and most commonly within less than 24 hours.

"Another anticancer therapy" is an anticancer therapy that is not a treatment with a compound of the first aspect of this invention. Such "another anticancer therapies" include chemotherapy; molecular targeted therapy; biologic therapy; and radiotherapy. These therapies are those used as monotherapy or in combination therapy.

Chemotherapeutic agents include:

alkylating agents, including:

alkyl sulfonates such as busulfan, ethyleneimine derivatives such as thiotepa, nitrogen mustards such as chlorambucil, cyclophosphamide, estramustine, ifosfamide, mechlorethamine, melphalan, and uramustine, nitrosoureas such as carmustine, lomustine, and streptozocin, triazenes such as dacarbazine, procarbazine, and temozolamide, and platinum compounds such as cisplatin, carboplatin, oxaliplatin, satraplatin, and picoplatin;

antimetabolites, including:

antifolates such as methotrexate, permetrexed, raltitrexed, and trimetrexate, purine analogs such as cladribine, chlorodeoxyadenosine, clofarabine, fludarabine, mercaptopurine, pentostatin, and thioguanine, pyrimidine analogs such as azacitidine, capecitabine, cytarabine, edatrexate, floxuridine, fluorouracil, gemcitabine, and troxacitabine;

natural products, including:

antitumor antibiotics such as bleomycin, dactinomycin, mithramycin, mitomycin, mitoxantrone, porfiromycin, and anthracyclines such as daunorubicin (including liposomal daunorubicin), doxorubicin (including liposomal doxorubicin), epirubicin, idarubicin, and valrubicin, enzymes such as L-asparaginase and PEG-L-asparaginase, microtubule polymer stabilizers such as the taxanes paclitaxel and docetaxel, mitotic inhibitors such as the vinca alkaloids vinblastine, vincristine, vindesine, and vinorelbine, topisomerase I inhibitors such as the camptothecins irinotecan and topotecan, and topoisomerase II inhibitors such as amsacrine, etoposide, and teniposide;

hormones and hormone antagonists, including:

androgens such as fluoxymesterone and testolactone, antiandrogens such as bicalutamide, cyproterone, flutamide, and nilutamide, aromatase inhibitors such as aminoglutethimide, anastrozole, exemestane, formestane, and letrozole, corticosteroids such as dexamethasone and prednisone, estrogens such as diethylstilbestrol, antiestrogens such as fulvestrant, raloxifene, tamoxifen, and toremifine, LHRH agonists and antagonists such as buserelin, goserelin, leuprolide, and triptorelin, progestins such as medroxyprogesterone acetate and megestrol acetate, and thyroid hormones such as levothyroxine and liothyronine; and miscellaneous agents, including altretamine, arsenic trioxide, gallium nitrate, hydroxyurea, levamisole, mitotane, octreotide, procarbazine, suramin, thalidomide, lenalidomide, photodynamic compounds such as methoxsalen and sodium porfimer, and proteasome inhibitors such as bortezomib.

Molecular targeted therapy agents include:

functional therapeutic agents, including:

gene therapy agents, antisense therapy agents, tyrosine kinase inhibitors such as erlotinib hydrochloride, gefitinib, imatinib mesylate, and semaxanib, and gene expression modulators such as the retinoids and rexinoids, e.g. adapalene, bexarotene, trans-retinoic acid, 9-cis-retinoic acid, and N-(4-hydroxyphenyl)retinamide;

phenotype-directed therapy agents, including:

monoclonal antibodies such as alemtuzumab, bevacizumab, cetuximab, ibritumomab tiuxetan, rituximab, and trastuzumab, immunotoxins such as gemtuzumab ozogamicin, and radioimmunoconjugates such as $^{131}$I-tositumomab; and cancer vaccines.

Biologic therapy agents include:

interferons such as interferon-$\alpha_{2a}$ and interferon-$\alpha_{2b}$, and interleukins such as aldesleukin, denileukin diftitox, and oprelvekin.

In addition to these agents intended to act against cancer cells, anticancer therapies include the use of protective or adjunctive agents, including:

cytoprotective agents such as amifostine, dexrazoxane, and mesna, phosphonates such as pamidronate and zoledronic acid, and stimulating factors such as epoetin, darbeopetin, filgrastim, PEG-filgrastim, and sargramostim.

Combination cancer therapy regimens with which the compounds of the first aspect of this invention may be combined include all regimens involving the use of two or more of the anticancer therapies (anticancer agents) such as those mentioned in paragraphs [0023] to [0025] above and/or radiotherapy, optionally including protective and adjunctive agents such as those mentioned in paragraph [0026] above; and the compound of the first aspect of this invention can be added to existing anticancer regimens known for the treatment of various cancers, such as the regimens mentioned in such books as Chabner and Longo, eds., "Cancer Chemotherapy and Biotherapy: Principles and Practice", 3rd ed. (2001), and Skeel, ed., "Handbook of Cancer Chemotherapy", 6th ed. (2003), both from Lippincott Williams & Wilkins, Philadelphia, Pa., U.S.A.; and regimens for anticancer therapies, especially chemotherapies, may be found on Web sites such as those maintained by the National Cancer Institute (www.cancer.gov), the American Society for Clinical Oncology (www.asco.org), and the National Comprehensive Cancer Network (www.nccn.org).

Many combination chemotherapeutic regimens are known to the art, such as combinations of platinum compounds and taxanes, e.g. carboplatin/paclitaxel, capecitabine/docetaxel, the "Cooper regimen", fluorouracil-levamisole, fluorouracil-leucovorin, methotrexate-leucovorin, and those known by the acronyms ABDIC, ABVD, AC, ADIC, AI, BACOD, BACOP, BVCPP, CABO, CAD, CAE, CAF, CAP, CD, CEC, CF, CHOP, CHOP+rituximab, CIC, CMF, CMFP, CyADIC, CyVADIC, DAC, DVD, FAC, FAC-S, FAM-S, FOLFOX-4, FOLFOX-6, M-BACOD, MACOB-B, MAID, MOPP, MVAC, PCV, T-5, VAC, VAD, VAPA, VAP-Cyclo, VAP-II, VBM, VBMCP, VIP, VP, and the like.

Combinations of chemotherapies and molecular targeted therapies, biologic therapies, and radiation therapies are also well known to the art; including therapies such as trastuzumab+paclitaxel, alone or in further combination with carboplatin, for certain breast cancers, and many other such regimens for other cancers; and the "Dublin regimen" and "Michigan regimen", both for esophageal cancer, and many other such regimens for other cancers.

"Comprising" or "containing" and their grammatical variants are words of inclusion and not of limitation and mean to specify the presence of stated components, groups, steps, and the like but not to exclude the presence or addition of other components, groups, steps, and the like. Thus "comprising" does not mean "consisting of", "consisting substantially of", or "consisting only of"; and, for example, a pharmaceutical composition "comprising" a compound must contain that compound but may also may contain other active ingredients and/or excipients.

Compounds of this Invention

In a first aspect, this invention is compounds of formula A:

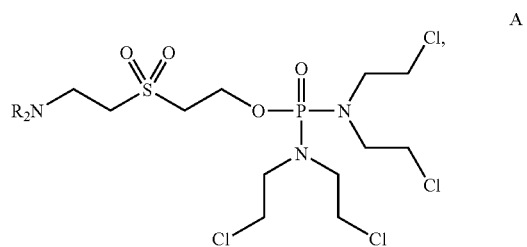

and their acid addition salts, where each R is independently methyl, ethyl, propyl, or isopropyl, or —NR$_2$ together is pyrrolidin-1-yl or piperidin-1-yl.

Representative compounds of the invention are those where each R is independently methyl, ethyl, or isopropyl; and where each R is the same; and where —NR$_2$ is dimethylamino (compound 1A), diethylamino (compound 2A), diisopropylamino (compound 3A), pyrrolidin-1-yl (compound 4A), or piperidin-1-yl (compound 5A), and their acid addition salts.

Acid addition salts (for example, pharmaceutically acceptable acid addition salts) of the compounds of formula A are included in the present invention and are useful in the compositions, methods, and uses described in this application. Suitable salts are those formed when inorganic acids (e.g. hydrochloric, hydrobromic, sulfuric, nitric, phosphoric, and chlorosulfonic acids) or organic acids (e.g. acetic, propionic, oxalic, malic, maleic, malonic, fumaric, citric, tartaric, lactic, succinic, and aceturic acids, and alkane- or arenesulfonic acids such as methanesulfonic, ethanesulfonic, 2-hydroxyethanesulfonic, benzenesulfonic, substituted benzenesulfonic such as chlorobenzenesulfonic and toluenesulfonic, naphthalenesulfonic and substituted naphthalenesulfonic, naphthalenedisulfonic and substituted naphthalenedisulfonic, and camphorsulfonic acids) react to form acid addition salts of the amine groups of the compounds. Such salts are preferably formed with pharmaceutically acceptable acids. See, for example, Stahl and Wermuth, eds., "Handbook of Pharmaceutically Acceptable Salts", (2002), Verlag Helvetica Chimica Acta, Zürich, Switzerland, for an extensive discussion of pharmaceutical salts, their selection, preparation, and use.

Preparation of the Compounds

Compounds of formula A may conveniently be prepared by:

(1) preparing the thioethyl phosphorodiamidates of formula B:

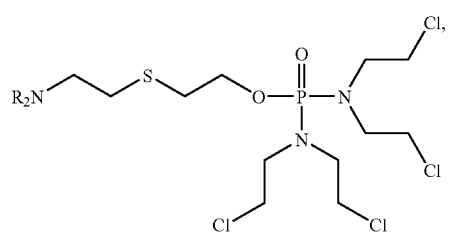

followed by oxidizing the sulfide to the corresponding sulfone [Method 1—as illustrated in Synthetic Examples 1 to 6]; or (2) preparing 2-[(2-hydroxyethyl)sulfonyl]ethyl N,N,N',N'-tetrakis(2-chloroethyl)-phosphorodiamidate, followed by converting the hydroxy group to a leaving group and reacting with an amine of the formula $R_2NH$ [Method 2—as illustrated in Synthetic Example 2].

Method 1 is shown below:

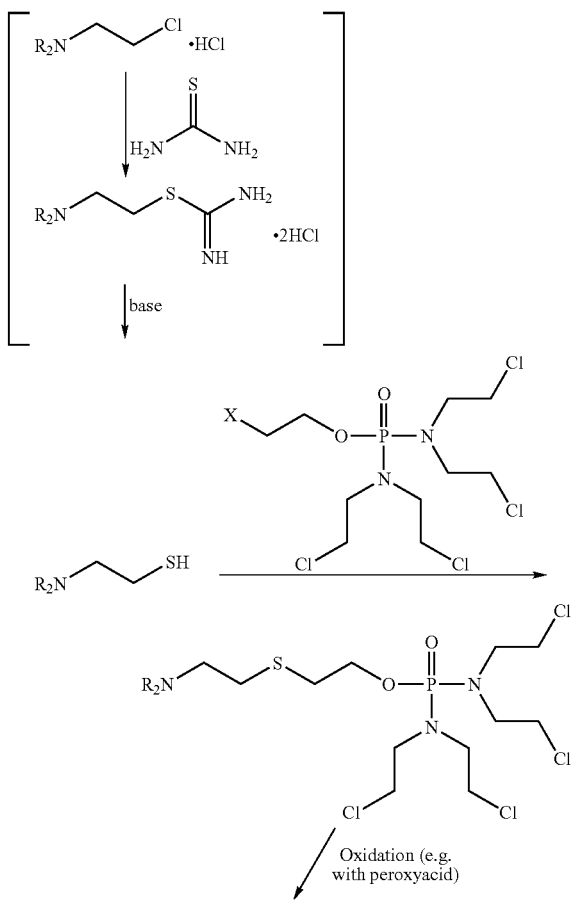

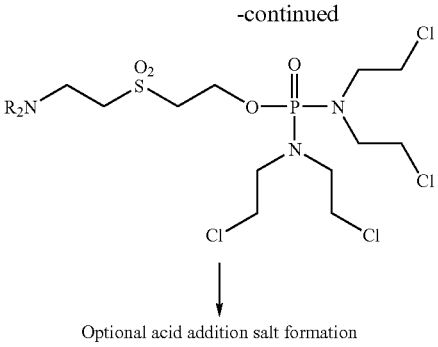

Optional acid addition salt formation

In the first step of Method 1, a 2-($NR_2$)-ethanethiol is converted into a 2-{[2-($NR_2$)ethyl]thio}ethyl N,N, N',N'-tetrakis(2-chloroethyl)phosphorodiamidate by reaction with a 2-X-ethyl N,N,N',N'-tetrakis(2-chloroethyl)phosphorodiamidate (where X is a leaving group such as Cl, Br, $C_{1-6}$ alkanesulfonyloxy, halo-$C_{1-6}$ alkanesulfonyloxy, or benzenesulfonyloxy optionally substituted with up to three substituents selected from halo, $C_{1-3}$ alkyl, halo-$C_{1-3}$ alkyl, $C_{1-3}$ alkyloxy, or halo-$C_{1-3}$ alkyloxy, such as methanesulfonyloxy, benzenesulfonyloxy, 4-bromobenzenesulfoxy, or 4-toluenesulfonyloxy). A typical procedure involves treating the 2-($NR_2$)-ethanethiol with a polar solvent such as water, an alkanol, dimethylformamide, or tetrahydrofuran, and a base such as a hydroxide, alkoxide, fluoride, or hydride, or a tertiary amine or amide base to form the thiolate anion, followed by adding the phosphorodiamidate. Thiolate displacement of the leaving group X of the phosphorodiamidate gives the 2-{[2-($NR_2$)ethyl]thio}ethyl N,N,N',N'-tetrakis(2-chloroethyl)-phosphorodiamidate.

2-(Dimethylamino)ethanethiol and 2-(diethylamino)ethanethiol are both readily commercially available as the hydrochloride salts. When the 2-($NR_2$)-ethanethiol is not available, it may be prepared by a method such as reacting a 2-($NR_2$)-ethyl halide [the chloride is shown in the reaction scheme] with thiourea to prepare a 2-($NR_2$)-ethylisothiourea, which may be isolated as an acid addition salt if desired. When the 2-($NR_2$)-ethylisothiourea is treated with base, the corresponding 2-($NR_2$)-ethanethiolate is formed in solution, and the resulting solution may be used directly in the formation of the 2-{[2-($NR_2$)ethyl]thio}ethyl N,N,N',N'-tetrakis(2-chloroethyl)phosphorodiamidate. A typical procedure involves treating a 2-($NR_2$)-ethyl chloride hydrochloride with thiourea in a lower alkanol, such as ethanol, at elevated temperature. On cooling, the isothiourea precipitates as a dihydrochloride salt, which may be isolated by filtration. The isothiourea is suspended in a lower alkanol and treated with base to form the thiolate anion, followed by adding the phosphorodiamidate. Thiolate displacement of the leaving group X of the phosphorodiamidate gives the 2-{[2-($NR_2$)ethyl]thio}ethyl N,N,N',N'-tetrakis(2-chloroethyl)phosphorodiamidate.

In the second step of Method 1, the 2-{[2-($NR_2$)ethyl]thio}ethyl N,N,N',N'-tetrakis(2-chloroethyl)phosphorodiamidate is oxidized to the corresponding 2-{[2-($NR_2$)ethyl]sulfonyl}ethyl N,N, N',N'-tetrakis(2-chloroethyl)phosphorodiamidate. This oxidation may be performed by any of the methods known in the art for the oxidation of sulfides to sulfones, such as the use of peracids (peroxycarboxylic acids), persulfates, perborates, peroxides, ozone, iodosyl reagents, halogens, and the like. Where a peracid is used, a typical procedure involves dissolving the 2-{[2-($NR_2$)

ethyl]thio}ethyl N,N,N',N'-tetrakis(2-chloroethyl)phosphorodiamidate in a solvent such as dichloromethane, acetic acid, or isopropyl acetate at reduced temperature, followed by the addition of the peracid (e.g. peracetic acid) in excess. The oxidation is performed under conditions that minimize oxidation of the amine nitrogen, such as by performing the oxidation at a sufficiently low pH to stabilize the amine as an ammonium cation.

Method 2 is shown below:

for the second step of Method 1 in paragraph [0040]; however, in Method 2 there is no risk of amine oxidation.

In the third step of Method 2, the hydroxy group of the 2-{[2-(hydroxy)ethyl]sulfonyl}ethyl N,N,N',N'-tetrakis(2-chloroethyl)phosphorodiamidate is esterified by reaction with a sulfonic acid anhydride, preferably one that gives a strong leaving group, such as the anhydrides of trifluoromethanesulfonic, fluorosulfonic, or pentafluorobenzenesulfonic acids. Typically, the 2-{[2-(hydroxy)ethyl]

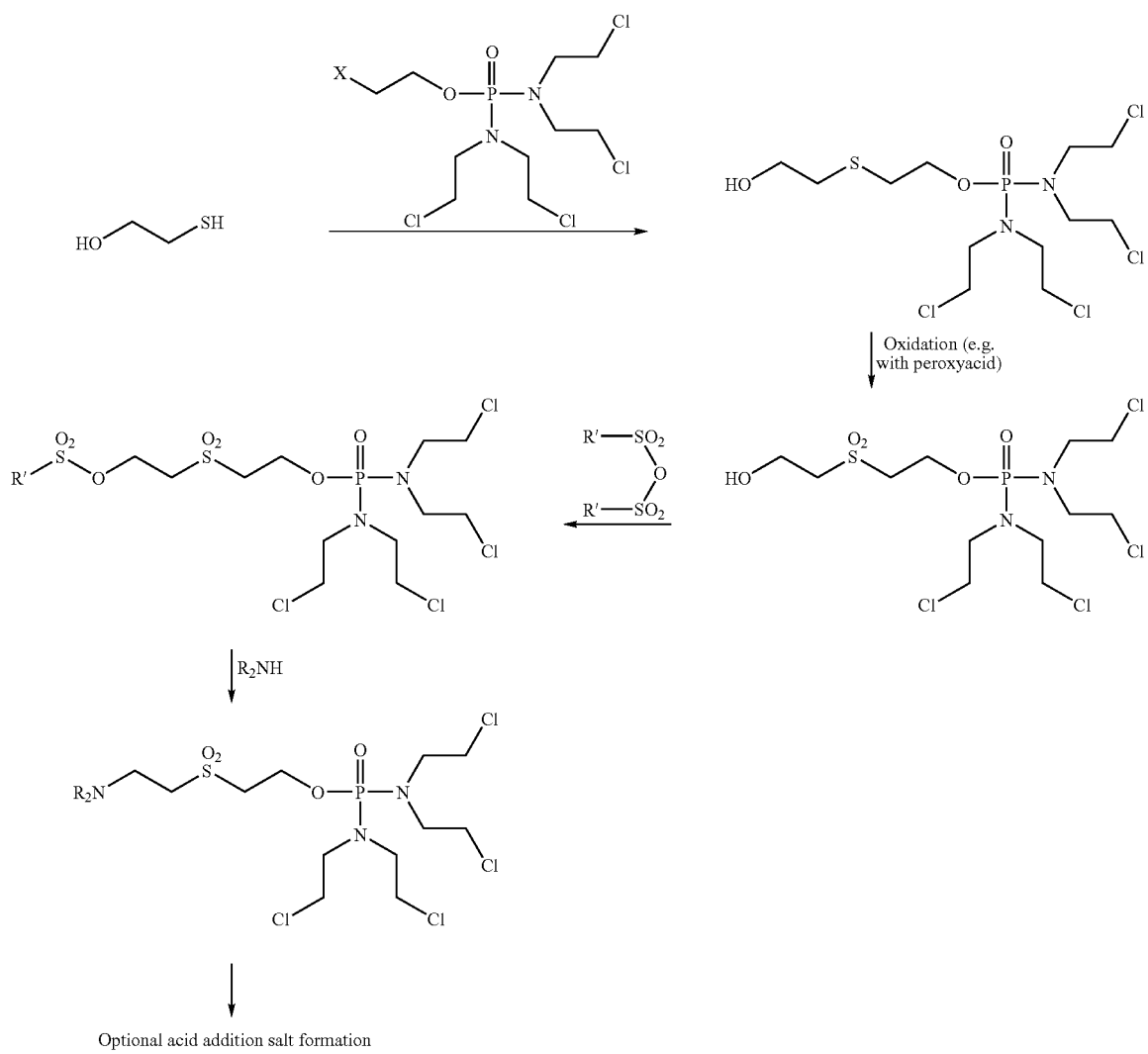

In the first step of Method 2, 2-mercaptoethanol is converted into 2-{[2-(hydroxy)ethyl]-thio}ethyl N,N,N',N'-tetrakis(2-chloroethyl)phosphorodiamidate by reaction with a 2-X-ethyl N,N,N',N'-tetrakis(2-chloroethyl)phosphorodiamidate (where X is as in the first step of Method 1 in paragraph [0038]). This reaction may be performed by any of the methods described for the first step of Method 1.

In the second step of Method 2, the 2-{[2-(hydroxy)ethyl] thio}ethyl N,N,N',N'-tetrakis(2-chloroethyl)phosphorodiamidate is oxidized to 2-{[2-(hydroxy)ethyl]sulfonyl}-ethyl N,N,N',N'-tetrakis(2-chloroethyl)phosphorodiamidate. This oxidation may be performed by any of the methods described sulfonyl}ethyl N,N,N',N'-tetrakis(2-chloroethyl)phosphorodiamidate is dissolved in a non-nucleophilic, preferably low-boiling, solvent such as dichloromethane, and the anhydride added, for example at 0° C. The sulfonate ester may be isolated if desired, but is more conveniently used directly in the next step.

In the fourth step of Method 2, the sulfonate ester is displaced with excess $R_2NH$. Typically, an excess of the amine is added to the solution from the third step and the reaction is allowed to proceed to completion. The 2-{[2-($NR_2$)ethyl] thio}ethyl N,N,N',N'-tetrakis(2-chloroethyl)phosphorodiamidate is conveniently isolated by addition of aqueous acid to the reaction mixture, removal of the organic layer, neutralization with a weak base (such as solid $NaHCO_3$), re-extraction of the 2-{[2-($NR_2$)ethyl]thio}ethyl N,N,N',N'-tetrakis(2-chloroethyl)phosphorodiamidate into an organic solvent, and removal of that solvent.

The compounds of formula A may be converted to acid addition salts by reaction with the appropriate acids, using techniques well known to a person of ordinary skill in the art for the formation of acid addition salts. The acid used, and the reaction conditions, may be chosen to give acid addition salts that are pharmaceutically acceptable and that have a form convenient for isolation and formulation, such as a solid form (for example, amorphous or crystalline).

Pharmaceutical Compositions and Administration

The second aspect of this invention is pharmaceutical compositions comprising a compound of the first aspect of this invention and optionally a pharmaceutically acceptable excipient.

The compounds of the first aspect of this invention may be administered by any route suitable to the subject being treated and the nature of the subject's condition. Routes of administration include administration by injection, including intravenous, intraperitoneal, intramuscular, and subcutaneous injection, by transmucosal or transdermal delivery, through topical applications, nasal spray, suppository and the like or may be administered orally. Pharmaceutical compositions may optionally be liposomal compositions, emulsions, compositions designed to administer the drug across mucosal membranes or transdermal compositions. Suitable compositions for each of these methods of administration may be found, for example, in Gennaro, ed., "Remington: The Science and Practice of Pharmacy", 20th ed. (2000), Lippincott Williams & Wilkins, Philadelphia, Pa., U.S.A. Typical compositions will be either oral or solutions for intravenous infusion. Typical dosage forms will be tablets (including coated tablets and "caplets") or capsules (including hard gelatin capsules and "softgels") for oral administration, solutions for intravenous infusion, and solids (especially lyophilized powders) for reconstitution as solutions for intravenous infusion.

Depending on the intended mode of administration, the pharmaceutical compositions may be in the form of solid, semi-solid or liquid dosage forms, preferably in unit dosage form suitable for single administration of a precise dosage. In addition to an effective amount of the active ingredient(s), the compositions may contain suitable pharmaceutically-acceptable excipients, including adjuvants which facilitate processing of the active compounds into preparations which can be used pharmaceutically. "Pharmaceutically acceptable excipient" refers to an excipient or mixture of excipients which does not interfere with the effectiveness of the biological activity of the active ingredient(s) and which is not toxic to the host to which it is administered.

For solid compositions, conventional excipients include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary excipients such as wetting or emulsifying agents, pH buffering agents and the like, for example, sodium acetate, sorbitan monolaurate, triethanolamine sodium acetate, triethanolamine oleate, etc.

For oral administration, the composition will generally take the form of a tablet or capsule, or it may be an aqueous or nonaqueous solution, suspension or syrup. Tablets and capsules are preferred oral administration forms. Tablets and capsules for oral use will generally include one or more commonly used excipients such as lactose and corn starch. Lubricating agents, such as magnesium stearate, are also typically added. When liquid suspensions are used, the active agent may be combined with emulsifying and suspending excipients. If desired, flavoring, coloring and/or sweetening agents may be added as well. Other optional excipients for incorporation into an oral composition include preservatives, suspending agents, thickening agents, and the like.

Injectable pharmaceutical compositions can be prepared in conventional forms, either as liquid solutions or suspensions, solid forms suitable for solubilization or suspension in liquid prior to injection, or as emulsions or liposomal compositions. The sterile injectable composition may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils, fatty esters or polyols are conventionally employed as solvents or suspending media.

The pharmaceutical compositions of this invention may also be formulated as lyophilized powders for parenteral administration. Powders may be reconstituted by addition of water or other primarily aqueous medium and then further diluted with a suitable diluent prior to use. The liquid composition is generally a buffered, isotonic, aqueous solution. Examples of suitable diluents are isotonic saline solution, aqueous 5% dextrose solution, and buffered sodium or ammonium acetate solution. Pharmaceutically acceptable solid or liquid excipients may be added to enhance or stabilize the composition, or to facilitate preparation of the composition.

Typically, a pharmaceutical composition of the present invention is packaged in a container with a label, or instructions, or both, indicating use of the pharmaceutical composition in the treatment of cancer.

The pharmaceutical composition may additionally contain one or more other pharmacologically active agents in addition to a compound of this invention. These additional active agents will typically be useful in treating cancer, or for enhancing the treatment of cancer by compounds of this invention.

Methods of Using the Compounds

The compounds of the first aspect of this invention have activity against human cancer cell lines, as demonstrated in the in vitro and in vivo Examples below, and are therefore considered to be useful as human cancer chemotherapeutic agents, for the treatment of human cancers.

Thus, the third aspect of this invention includes methods of treating cancer in humans by administering a therapeutically effective amount of a compound of the first aspect of this invention, or a pharmaceutical composition of the second aspect of this invention, to the human; and the use of the compounds of the first aspect of this invention in the manufacture of medicaments for the treatment of cancer in humans. Optionally, the methods further comprise treating the human with another anticancer therapy, such as a therapy already conventional for the cancer being treated.

Cancers that are particularly treatable by the method of this invention are cancers with sensitivity to inducers of apoptosis, and more specifically those cancers that express or, particularly, overexpress one or more glutathione S-transferase isoenzymes. Cancers that express or overexpress one or more glutathione S-transferase isoenzymes when treated with other anticancer compounds or combination cancer chemotherapy regimens are especially treatable by the method of this invention. Such cancers include cancers of the brain, breast, bladder, cervix, colon and rectum, esophagus, head and neck, kidney, lung, liver, ovary, pancreas, prostate, and stomach; leukemias such as ALL, AML, AMML, CLL, CML, CMML, and hairy cell leukemia; Hodgkin's and non-Hodgkin's lymphomas; mesotheliomas, multiple myeloma; and sarcomas of bone and soft tissue. Cancers particularly treatable by the method of this invention include breast, ovarian, colorectal, and non-small cell lung cancers.

The amount of the compound of the first aspect of this invention that is administered to the human (either alone or, more usually, in a composition of the second aspect of this invention) should be a therapeutically effective amount when used alone or when used in conjunction with the another anticancer therapy (if the compound of the first aspect of this invention is administered in conjunction with another anticancer therapy); and similarly the amount of the another anticancer therapy that is administered to the mammal (if the compound of the first aspect of this invention is administered in conjunction with another anticancer therapy) should be a therapeutically effective amount when used in conjunction with the compound of the first aspect of this invention. However, the therapeutically effective amount of either the compound of the first aspect of this invention and the amount of the another anticancer therapy when administered in combination cancer chemotherapy may each be less than the amount which would be therapeutically effective if delivered to the human alone. It is common in cancer therapy, though, to use the maximum tolerated dose of the or each therapy, with a reduction only because of common toxicity of the therapies used or potentiation of the toxicity of one therapy by another. Because of the lack of cross-resistance of canfosfamide, for example, with several common chemotherapeutic agents, and its relative lack of clinically severe toxicity, especially its lack of clinically severe hematological toxicity, it is expected that compounds of the first aspect of this invention will be administrable at essentially their maximum tolerated dose as a single agent, and no reduction in the amount of the another anticancer therapy will be required.

The compounds of the first aspect of this invention, or pharmaceutical compositions of the second aspect of this invention, are thus used to treat cancer in humans requiring such treatment, by administering a therapeutically effective amount of the chosen compound or composition. Therapeutically effective amounts of compounds of the invention are in the range of 10-10,000 mg/m$^2$, for example, 30-3000 mg/m$^2$ or 100-1000 mg/m$^2$. Dosing may be at 1-35 day intervals; for example, about 500-1000 mg/m$^2$ at 1-5 week intervals, especially at 1, 2, 3, or 4 week intervals, or at higher frequencies including as frequently as once/day for several (e.g. 5 or 7) days, with the dosing repeated every 2, 3, or 4 weeks, or constant infusion for a period of 6-72 hours, also with the dosing repeated every 2, 3, or 4 weeks. Suitable dosages and dose frequencies will be readily determinable by a person of ordinary skill in the art having regard to that skill and this disclosure. No unacceptable toxicological effects are expected when compounds of the invention are administered in accordance with the present invention.

Suitable dosing for the other anticancer therapy (if the compound of the first aspect of this invention is used in combination) will be the dosing already established for that therapy, as described in such documents as those listed in paragraph [0027]. Such dosing varies widely with the therapy: for example, capecitabine (2500 mg/m$^2$ orally) is dosed twice daily for 2 weeks on and 1 week off, imatinib mesylate (400 or 600 mg/day orally) is dosed daily, rituximab is dosed weekly, paclitaxel (135-175 mg/m$^2$) and docetaxel (60-100 mg/m$^2$) are dosed weekly to every three weeks, carboplatin (4-6 mg/mL-min) is dosed once every 3 or 4 weeks (though the doses may be split and administered over several days), nitrosourea alkylating agents such as carmustine are dosed as infrequently as once every 6 weeks. Radiotherapy may be administered as frequently as weekly (or even within that split into smaller dosages administered daily).

A person of ordinary skill in the art of cancer therapy will be able to ascertain a therapeutically effective amount of the compound of the first or second aspect of this invention and a therapeutically effective amount of another anticancer therapy for a given cancer and stage of disease without undue experimentation and in reliance upon personal knowledge and the disclosure of this application.

Combination therapies include the combination administration of a compound of the first aspect of this invention with a platinum compound such as carboplatin or cisplatin, optionally in further combination with gemcitabine or a taxane such as docetaxel or paclitaxel; with gemcitabine; with a taxane; with an anthracycline such as doxorubicin or liposomal doxorubicin; with oxaliplatin, optionally in further combination with capecitabine or fluorouracil/leucovorin; and with gemcitabine or a platinum compound such as carboplatin or cisplatin, in further combination with a vinca alkaloid such as vinorelbine.

EXAMPLES

The following examples illustrate the preparation of compounds of this invention, and their activity in predictive in vitro and in vivo anticancer assays.

Synthetic Examples

The compounds of this invention are prepared by conventional methods of organic chemistry. See, for example, Larock, "Comprehensive Organic Transformations", (1989), Wiley-VCH, New York, N.Y., U.S.A. The compounds of this invention can be synthesized, generally following the synthetic schemes illustrated earlier in this application, as shown in the following examples or by modifying the exemplified synthesis by means known to those of ordinary skill in the art.

Synthetic Example 1

Preparation of 2-{[2-(diisopropylamino)ethyl] sulfonyl}ethyl N,N,N',N'-tetrakis(2-chloroethyl) phosphorodiamidate, compound 3A, as its hydrochloride salt 2-{[2-(Diisopropylamino)ethyl]thio}ethyl N,N,N',N'-tetrakis(2-chloroethyl)phosphorodiamidate. A mixture of 2-(diisopropylamino)ethyl chloride hydrochloride (1.0 g, 5.0 mmol) and thiourea (380 mg, 5.0 mmol, 1.0 eq.) in ethanol (4 mL) was heated to 120° C. for 5 minutes and then allowed to cool down to room temperature. The white precipitate of 2-(diisopropylamino)ethylisothiouronium dihydrochloride that formed was filtered, washed with ethanol, placed in a round-bottomed flask containing methanol (50 mL), and treated with sodium hydroxide (5.0 mL of 4M solution in methanol, 20 mmol, 4.0 eq.). The mixture was stirred at room temperature for 30 minutes and 2-(4-bromobenzenesulfonyloxy)ethyl N,N,N',N'-tetrakis(2-chloroethyl)phosphorodiamidate (7.0 mL of 0.7M solution in toluene, 4.9 mmol, 0.98 eq.) was added. The mixture was stirred at room temperature until all the 2-(4-bromobenzenesulfonyloxy)ethyl N,N,N',N'-tetrakis(2-chloroethyl)phosphorodiamidate was consumed, as determined by HPLC-ELSD (Evaporative Light Scattering Detection). The mixture was acidified to pH 7 with 1.0 M aqueous $H_3PO_4$ and concentrated under vacuum to a thick slurry. The slurry was taken up in ethyl acetate (800 mL) and washed with 5% aqueous $NaHCO_3$ (2×800 mL). The organic layer was separated, dried over anhydrous $MgSO_4$, filtered, and concentrated under vacuum to give 2-{[2-(diisopropylamino)ethyl]thio}ethyl N,N,N',N'-tetrakis(2-chloroethyl)phosphorodiamidate as a clear oil (2.3 g, 86% yield).

2-{[2-(Diisopropylamino)ethyl]sulfonyl}ethyl N,N,N',N'-tetrakis(2-chloroethyl)phosphorodiamidate hydrochloride. A solution of 2-{[2-(diisopropylamino)ethyl]thio}ethyl N,N,N',N'-tetrakis(2-chloroethyl)phosphorodiamidate (2.3 g, 4.3 mmol) in dimethylformamide (30 mL) at 0° C. was treated with trifluoroacetic acid (1.6 mL, 21.5 mmol, 5.0 eq.) and stirred at 0° C. for an additional 10 minutes. Peracetic acid (726 μL of a 32%/wt solution in acetic acid, 10.8 mmol, 2.5 eq.) was added over 5 minutes, then the mixture was allowed to warm to room temperature. Stirring was continued until analysis of an aliquot by LC/MS indicated complete conversion of 2-{[2-(diisopropylamino)ethyl]thio}ethyl N,N,N',N'-tetrakis(2-chloroethyl)phosphorodiamidate to 2-{[2-(diisopropylamino)ethyl]sulfonyl}ethyl N,N,N',N'-tetrakis(2-chloroethyl)phosphorodiamidate (typically about 2 hours). The reaction mixture was diluted with ethyl acetate (800 mL) and washed with a 1:1 mixture of 0.2M aqueous $Na_2S_2O_4$ and saturated aqueous $NaHCO_3$ (2×800 mL). The organic layer was separated, dried over anhydrous $MgSO_4$, filtered, and treated with excess hydrochloric acid (4.0M in dioxane). The resulting hazy solution was concentrated under vacuum to give 2-{[2-(diisopropylamino)ethyl]sulfonyl}ethyl N,N,N',N'-tetrakis(2-chloroethyl)-phosphorodiamidate hydrochloride as a clear oil (2.53 g, 100% yield). MS (ES$^+$): m/z=564 [$C_{18}H_{39}Cl_4N_3O_4PS$+H]; $^1$H NMR (CD$_3$OD): δ=1.44 (t, J=6.3 Hz, 12H), 3.41-3.52 (m, 8H), 3.64-3.87 (m, 16H), 4.53 (q, J=5.5 Hz, 2H); $^{31}$P NMR (CD$_3$OD): δ=18.01.

Synthetic Example 2

Preparation of 2-{[2-(pyrrolidin-1-yl)ethyl]sulfonyl}ethyl N,N,N',N'-tetrakis(2-chloroethyl)phosphorodiamidate, compound 4A, as its hydrochloride salt 2-{[2-(Pyrrolidin-1-yl)ethyl]sulfonyl}ethyl N,N,N',N'-tetrakis(2-chloroethyl)phosphorodiamidate was prepared from 1-(2-chloroethyl)pyrrolidine hydrochloride using the procedure of Synthetic Example 1. MS (ES$^+$): m/z=536 [$C_{16}H_{33}Cl_4N_3O_4PS$+H]; $^1$H NMR (CD$_3$OD): δ=2.02-2.09 (m, 2H), 2.15-2.22 (m, 2H), 3.15-3.22 (m, 2H), 3.42-3.53 (m, 8H), 3.68-3.75 (m, 16H), 4.51 (dd, J=5.5, 5.9 Hz, 2H); 31P NMR (CD$_3$OD): δ=18.01.

Synthetic Example 3

Preparation of 2-{[2-(piperidin-1-yl)ethyl]sulfonyl}ethyl N,N,N',N'-tetrakis(2-chloroethyl)phosphorodiamidate, compound 5A, as its hydrochloride salt 2-{[2-(Piperidin-1-yl)ethyl]sulfonyl}ethyl N,N,N',N'-tetrakis(2-chloroethyl)phosphorodiamidate was prepared from 1-(2-chloroethyl)piperidine hydrochloride using the procedure of Synthetic Example 1. MS (ES$^+$): m/z=548 [$C_{17}H_{35}Cl_4N_3O_4PS$+H]; $^1$H NMR (CD$_3$OD): δ=1.50-1.58 (m, 1H), 1.74-1.88 (m, 3H), 1.94-2.04 (m, 2H), 3.04 (t, J=3.1 Hz, 2H), 3.41-3.52 (m, 8H), 3.61-3.77 (m, 16H), 4.51 (dd, J=5.5, 6.3 Hz, 2H).

Synthetic Example 4

Preparation of 2-{[2-(diethylamino)ethyl]sulfonyl}ethyl N,N,N',N'-tetrakis(2-chloroethyl)phosphorodiamidate, compound 2A, as its hydrochloride salt To a solution of 2-(diethylamino)ethanethiol hydrochloride (840 g, 5 mmol) in methanol (20 mL) was added NaOH (3.8 mL of 4M solution in methanol, 15 mmol, 3 eq.) and 2-(4-bromobenzenesulfonyloxy)ethyl N,N,N',N'-tetrakis(2-chloroethyl)phosphorodiamidate (7.0 mL of 0.7M solution in toluene, 4.9 mmol, 0.98 eq.). The mixture was stirred at room temperature until all the 2-(4-bromobenzenesulfonyloxy)ethyl N,N,N',N'-tetrakis(2-chloroethyl)phosphorodiamidate was consumed, as determined by HPLC-ELSD. The mixture was acidified to pH 7 with 1.0 M aqueous $H_3PO_4$ and concentrated under vacuum to a thick slurry. The slurry was taken up in ethyl acetate (400 mL) and washed with 5% aqueous $NaHCO_3$ (2×400 mL) and then with aqueous HCl (2×400 mL). The acidic aqueous layers were combined and brought to pH>9 with solid $NaHCO_3$, then extracted with ethyl acetate (2×800 mL). The ethyl acetate solution was separated, dried over anhydrous $MgSO_4$, filtered, and concentrated under vacuum to give 2-{[2-(diethylamino)ethyl]thio}ethyl N,N,N',N'-tetrakis(2-chloroethyl)phosphorodiamidate as a clear oil (1.05 g, 42% yield). The 2-{[2-(diethylamino)ethyl]thio}ethyl N,N,N',N'-tetrakis(2-chloroethyl)phosphorodiamidate was oxidized to 2-{[2-(diethylamino)ethyl]sulfonyl}ethyl N,N,N',N'-tetrakis(2-chloroethyl)phosphorodiamidate and isolated as the hydrochloride salt using the procedure of Synthetic Example 1. MS (ES$^+$): m/z=536 [$C_{16}H_{35}Cl_4N_3O_4PS$+H]; $^1$H NMR (CD$_3$OD): δ=1.36 (t, J=7.4 Hz, 6H), 3.28-3.34 (m, 2H), 3.40-3.50 (m, 10H), 3.65-3.77 (m, 14H), 4.51 (dd, J=5.1, 6.3 Hz, 2H); $^{31}$P NMR (CD$_3$OD): δ=18.02.

Synthetic Example 5

Preparation of 2-{[2-(dimethylamino)ethyl]sulfonyl}ethyl N,N,N',N'-tetrakis(2-chloroethyl)phosphorodiamidate, compound 1A, as its hydrochloride salt 2-{[2-(Dimethylamino)ethyl]sulfonyl}ethyl N,N,N',N'-tetrakis(2-chloroethyl)-phosphorodiamidate was prepared from 2-(dimethylamino)ethanethiol hydrochloride using the procedure of Synthetic Example 4. MS (ES$^+$): m/z=508 [$C_{14}H_{31}Cl_4N_3O_4PS$+H]; $^1$H NMR (CD$_3$OD): δ=2.98 (s, 6H), 3.30-3.31 (m, 4H), 3.43-3.50 (m, 8H), 3.66-3.77 (m, 14H), 4.51 (dd, J=5.1, 6.7 Hz, 2H); $^{31}$P NMR (CD$_3$OD): δ=18.08.

Synthetic Example 6

Preparation of 2-{[2-(diethylamino)ethyl]sulfonyl}ethyl N,N,N',N'-tetrakis(2-chloroethyl)phosphorodiamidate, compound 2A, as its citrate salt 2-{[2-(Diethylamino)ethyl]sulfonyl}ethyl N,N,N',N'-tetrakis(2-chloroethyl)-phosphorodiamidate. To a 5 L three-neck flask equipped with an overhead stirrer, thermometer, and 1 L addition funnel was added 2-(diethylamino)

ethanethiol hydrochloride (170 g, 447 mmol). A solution of NaOH (42.0 g, 1.05 mol) in methanol (480 mL) was added and the resulting solution cooled to 5° C. in an ice bath. 2-(4-Bromobenzenesulfonyloxy)ethyl N,N,N',N'-tetrakis(2-chloroethyl)phosphorodiamidate, (320 g of 50% solution in toluene, 263 mmol) was placed in a 1 L flask and the solvent removed under vacuum. The resulting oil was dissolved in methanol (320 mL) and added dropwise to the reaction mixture over 50 minutes, while maintaining the temperature below 10° C., after which time a white solid precipitate formed. The resulting white slurry was stirred at 10-20° C. for 4 hours and then at room temperature for an additional 2 hours. Analysis by HPLC-ELSD indicated the reaction was >95% complete based on the disappearance of 2-(4-bromobenzenesulfonyloxy)ethyl N,N,N',N'-tetrakis(2-chloroethyl)phosphorodiamidate and appearance of the 2-{[2-(diethylamino)ethyl]thio}ethyl N,N,N',N'-tetrakis(2-chloroethyl)phosphorodiamidate product. The reaction mixture was filtered to remove the white precipitate, and the solvent from the filtrate removed under vacuum. The resulting viscous white oil was dissolved in ethyl acetate (3000 mL) and washed with water (2×1500 mL). This solution was placed in a 5 L three-neck flask equipped with an over head stirrer, thermometer, and a 1 L addition funnel containing a solution of 2 $KHSO_5.KHSO_4.K_2SO_4$ (Oxone®) (257.0 g, 418 mmol) in water (1 L). The Oxone® was added in approximately 250 mL portions over 3 hours with conversion of the 2-{[2-(diethylamino)ethyl]thio}ethyl N,N,N',N'-tetrakis(2-chloroethyl)phosphorodiamidate to 2-{[2-(diethylamino)ethyl]sulfonyl}ethyl N,N,N',N'-tetrakis(2-chloroethyl)phosphorodiamidate monitored by HPLC-ELSD analysis of the biphasic reaction mixture. Once the reaction was complete, as measured by disappearance of the sulfide and intermediate sulfoxide and appearance of the product, the reaction was quenched by addition of $Na_2S_2O_4$ (400 mL of 1M aqueous solution). The organic layer was removed and washed with water (2×1 L) and 1M aqueous NaOH (2×1 L), then evaporated to dryness under vacuum to give 2-{[2-(diethylamino)ethyl]sulfonyl}ethyl N,N,N',N'-tetrakis(2-chloroethyl)phosphorodiamidate as a clear oil (128.5 g, 91% yield), 95% pure by HPLC-ELSD.

2-{[2-(Diethylamino)ethyl]sulfonyl}ethyl N,N,N',N'-tetrakis(2-chloroethyl)-phosphorodiamidate citrate. To a solution of 2-{[2-(diethylamino)ethyl]sulfonyl}ethyl N,N,N',N'-tetrakis(2-chloroethyl)phosphorodiamidate (90.0 g, 167.5 mmol) in ethyl acetate (300 mL) was added a solution of citric acid (167.5 mL of 1M ethanol solution, 167.5 mmol) with vigorous stirring. After stirring at room temperature for 6 hours the reaction mixture became a beige, viscous slurry. Filtration, washing the precipitate with ethyl acetate, and drying under high vacuum gave the citrate salt as a white, amorphous powder (80 g, 65.5% yield for first crop), 98% pure by HPLC-ELSD. MS (ES$^+$): m/z=536 [$C_{16}H_{35}Cl_4N_3O_4PS$+H].

Synthetic Example 7

Preparation of 2-{[2-(diethylamino)ethyl] sulfonyl}ethyl N,N,N',N'-tetrakis(2-chloroethyl) phosphorodiamidate, compound 2A, as its hydrochloride salt, by Method 2

2-{[2-(Hydroxy)ethyl]thio}ethyl N,N,N',N'-tetrakis(2-chloroethyl)phosphorodiamidate. 2-mercaptoethanol (400 μL, 5.7 mmol) was dissolved in methanol (8 mL), and NaOH in methanol, (3.56 mL of 4M, 14.25 mmol) was added. The solution was cooled to 0° C. and 2-(4-bromobenzenesulfonyloxy)ethyl N,N,N',N'-tetrakis(2-chloroethyl)phosphorodiamidate (8.35 mL of 0.82M solution in toluene, 6.84 mmol) was added, and the reaction mixture allowed to warm to room temperature. After 12 hours, the mixture was filtered, neutralized to pH 7 with 1M aqueous $H_3PO_4$, and concentrated under vacuum to a thick syrup. This syrup was diluted with isopropyl acetate (200 mL), and washed with water (3×200 mL). The isopropyl acetate layer was dried over $MgSO_4$, filtered, and concentrated under vacuum to give a clear oil. This oil was purified on a 30 mm×150 mm silica gel column using a gradient of 70:30 ethyl acetate/hexanes to 100% ethyl acetate to give 2-{[2-(hydroxy)ethyl]thio}ethyl N,N,N',N'-tetrakis(2-chloroethyl)phosphorodiamidate as a clear oil (1.41 g, 55% yield). $^1$H NMR (CDCl$_3$): δ 1.64 (bs, 1H), 2.76 (t, 2H, J=5.9 Hz), 2.84 (t, 2H, J=6.3 Hz), 3.40-3.47 (m, 8H), 3.62-3.69 (m, 8H), 3.76 (t, 2H, J=5.9 Hz), 4.18-4.23 (m, 2H); $^{31}$P NMR (CDCl$_3$): δ 17.58.

2-{[2-(Hydroxy)ethyl]sulfonyl}ethyl N,N,N',N'-tetrakis(2-chloroethyl)phosphorodiamidate. 2-{[2-(Hydroxy)ethyl]thio}ethyl N,N,N',N'-tetrakis(2-chloroethyl)phosphorodiamidate (4.53 g, 10 mmol) was dissolved in isopropyl acetate (10 mL) and cooled to 0° C., and peracetic acid (32% in acetic acid, 8 mL, 30 mmol) was added over 5 minutes. The reaction mixture was allowed to warm to room temperature and kept for 3 hours. The reaction mixture was diluted with isopropyl acetate (200 mL) and washed with 0.1M aqueous $Na_2S_2O_3$ (2×200 mL) and water (200 mL). The isopropyl acetate layer was dried over $MgSO_4$, filtered, and concentrated under vacuum to give 2-{[2-(hydroxy)ethyl]sulfonyl}ethyl N,N,N',N'-tetrakis(2-chloroethyl)phosphorodiamidate as a clear oil (3.89 g, 81% yield). MS (ES+): m/z=481 [$C_{12}H_{25}Cl_4N_2O_5PS$+H]; $^1$H NMR (DMSO-d$^6$): δ 3.26-3.36 (m, 12H), 3.67-3.82 (m, 10H), 4.28 (dd, J=5.9, 6.3 Hz, 2H), 5.19 (t, J=5.1 Hz, 1H); $^{31}$P NMR (DMSO-d$^6$): δ 17.22.

2-{[2-(Diethylamino)ethyl]sulfonyl}ethyl N,N,N',N'-tetrakis(2-chloroethyl)phosphorodiamidate hydrochloride. 2-{[2-(Hydroxy)ethyl]sulfonyl}ethyl N,N,N',N'-tetrakis(2-chloroethyl)phosphorodiamidate (150 mg, 0.31 mmol) was dissolved in dichloromethane (2 mL) and cooled to 0° C., and N,N-diisopropylethylamine (108 μL, 0.62 mmol) and trifluoromethanesulfonic anhydride (55 μL, 0.33 mmol) were added, and the reaction mixture allowed to stand for 15 minutes. The reaction mixture was added to a solution of diethylamine (64 μL, 0.62 mmol) in isopropyl acetate (2 mL), and this was allowed to stand for 30 minutes. The reaction mixture was diluted with isopropyl acetate (10 mL) and washed with 5% aqueous NaHCO$_3$ (2×10 mL) and 1M aqueous HCl (2×5 mL). The aqueous acidic fractions were combined, washed with dichloromethane (10 mL), and solid NaHCO$_3$ was added to pH>9. The mixture was extracted with isopropyl acetate (2×10 mL), and the isopropyl acetate extracts combined, dried over MgSO$_4$, filtered, diluted with HCl (4.0M in dioxane, 1 mL), and concentrated under vacuum to give 2-{[2-(diethylamino)ethyl]sulfonyl}ethyl N,N,N',N'-tetrakis(2-chloroethyl)phosphorodiamidate hydrochloride as a pale brown oil (32 mg, 19% yield). MS (ES$^+$): m/z=536 [$C_{16}H_{34}Cl_4N_3O_4PS$+H].

Other compounds of formula A may be similarly prepared. The citrate salt of compound 1A was prepared as a solid by treating compound 1A with citric acid using methods similar to those used to prepare the citrate salt of compound 2A, while the hydrochloride salt (Synthetic Example 5) was prepared as an oil. The fumarate, tartrate, and p-toluenesulfonate salts of compound 2A were prepared as solids, and the maleate, methanesulfonate, phosphate, succinate, and sulfate salts prepared as oils, by reacting compound 2A with the corresponding acids using methods similar to those used to prepare the citrate salt, while the hydrochloride salt (Synthetic Example 4) was prepared as an oil. The citrate, fumarate, hydrochloride, maleate, methanesulfonate, phosphate, succinate, and sulfate salts of compound 3A were prepared as oils by similar methods, as was the hydrochloride salt (Synthetic Example 1). The citrate and tartrate salts of compound 5A were prepared as solids, and the maleate, succinate, and p-toluenesulfonate salts as oils, by similar methods, and the hydrochloride salt (Synthetic Example 3) was prepared as a solid. Other salts of compounds of formula A may similarly be prepared by using the appropriate acids, preferably in solvents that permit the isolation of the acid addition salts as solids.

The hydrochloride salt of compound 2A had a solubility in water of at least 50 mg/mL, the citrate salt had a solubility of about 19 mg/mL, and the tartrate salt was slightly more soluble than the citrate salt. The hydrochloride salt of compound 1A was also highly soluble in water, while the citrate salt was somewhat more soluble than the citrate salt of compound 2A.

In vitro Example 1

Cytotoxicity/Growth Inhibition Assay

The following examples illustrate the beneficial effect of the compounds of this invention against human cancer cell lines in vitro. These results are considered predictive of efficacy in human cancer chemotherapy, as other anticancer agents tested in these assays have shown anticancer activity in humans.

The human cancer cell lines DLD-1 (colorectal adenocarcinoma), LNCaP (prostate carcinoma), and MIA PaCa-2 (pancreatic carcinoma) were obtained from the American Type Culture Collection, Manassas, Va., U.S.A., and MX-1 (breast carcinoma) from the National Cancer Institute, Bethesda, Md., U.S.A. The CellTiter-Glo assay kit was obtained from Promega Corporation, Madison, Wis., U.S.A. All products were used in accordance with manufacturer's directions. All assays were conducted in triplicate wells, with dimethyl sulfoxide (DMSO) solvent control. The extent of cell growth was expressed as a percentage of the signal from the solvent control wells.

Log-phase cells were trypsinized, collected by centrifugation, and resuspended in a small volume of fresh medium, and the density of viable cells was determined following Trypan Blue staining. Cells were diluted in fresh media ($3 \times 10^3$ cells/mL for DLD-1, MIA PaCa-2, and MX-1, and $6 \times 10^3$ cells/mL for LNCaP), and added at 150 µL/well to 96-well plates, and incubated for several hours to allow attachment in the case of adherent cells. Compounds 1A to 5A, as their hydrochloride salts, dissolved in DMSO, was diluted 50-fold with fresh medium and the diluted solutions immediately added at 50 µL/well to the cell suspensions, giving final compound concentrations between 0.1 µM and 200 µM and a final DMSO concentration of 0.5%. The cells were cultured for approximately three doubling times (3 days for MIA PaCa-2 and MX-1, and 4 days for DLD-1 and LNCaP). The cells were then collected by centrifugation, and 100 µL of the culture supernatant was replaced by the CellTiter-Glo reagent. After incubation for 10 minutes at room temperature, and the plate was read with a luminometer. A number of compounds of formula A were tested in this assay and found to be active. The compounds were found to be of similar potency to canfosfamide, with compounds 2A and 3A being more potent in all assays.

Compounds of formula A showed the following activity in this assay:

| Compound | $IC_{50}$ (DLD-1), µM | $IC_{50}$ (LNCaP), µM | $IC_{50}$ (MIA PaCa-2), µM | $IC_{50}$ (MX-1), µM |
|---|---|---|---|---|
| 1A | 11 | 130 | 39 | 43 |
| 2A | 7.9 | 75 | 16 | 16 |
| 3A | 5.0 | 16 | 6.8 | 5.0 |
| 4A | 8.6 | 100 | 29 | 26 |
| 5A | 13 | 140 | 36 | 41 |

In Vivo Examples

In vivo Example 1

MX-1 Xenograft Assay, Intraperitoneal Administration

Female athymic nu/nu mice (Harlan, Indianapolis, Ind., U.S.A. or similar vendor), 6-8 weeks old (approximately 20 g), were implanted in the mammary fat pad of the right fore flank with 20-30 mg pieces of MX-1 tumor harvested from similar nu/nu mice that had previously been implanted with the MX-1 tumor. Approximately 7-10 days after tumor transplantation, when the tumor weight was approximately 50-200 mg, the mice were assigned to treatment groups such that each treatment group had a similar average tumor weight at the start of treatment. Groups of mice were treated with compounds 2A and 3A at 50 mg/Kg and compounds 1A, 2A, 3A, and 5A at 100 mg/Kg, in all cases as the hydrochloride salts dissolved in aqueous 5% dextrose, by intraperitoneal injection once/day for 5 consecutive days, with vehicle control. Tumor mass, estimated from volume, was measured twice weekly; and tumor growth inhibition was measured when the average tumor mass in the control group first exceeded 2000 mg. All compounds were active in this assay, with tumor growth inhibition compared to vehicle of 70% and 23% for compounds 2A and 3A, respectively, at 50 mg/Kg, and 100%, 100%, 100%, and 91% for compounds 1A, 2A, 3A, and 5A, respectively, at 100 mg/Kg.

In Vivo Example 2

MX-1 Xenograft Assay, Oral Administration

A study similar to that described in In vivo Example 1 was performed using oral administration of compounds 2A and 3A. Groups of mice were treated with compound 2A at 100, 150, 200, or 300 mg/Kg, or compound 3A at 150 mg/Kg, in each case as the hydrochloride salts dissolved in water, by gavage once/day for 5 consecutive days, with vehicle control. Both compounds were active in this assay and compound 2A caused dose-dependent tumor inhibition. Compound 2A caused a dose-dependent inhibition of tumor growth between 92% (100 mg/Kg) and 100% (300 mg/Kg) compared to vehicle, and compound 3A caused an inhibition of 98% (150 mg/Kg).

In Vivo Example 3

MX-1 Xenograft Assay, Intravenous Administration

A study similar to that described in In vivo Example 1 was performed using intravenous administration of compound 2A. A group of mice was treated with the compound, as the hydrochloride salt dissolved in aqueous 5% dextrose, at 40 and 80 mg/Kg by tail vein injection once/day for 5 consecutive days, with vehicle control. Compound 2A was active in this assay, causing 53% (40 mg/Kg) and 99% (80 mg/Kg) inhibition of tumor growth compared to vehicle.

In Vivo Example 4

MiaPaCa-2 Xenograft Assay, Intraperitoneal Administration

Male athymic nu/nu mice, 6-8 weeks old (approximately 20 g), were implanted subcutaneously in the right fore flank with 20-30 mg pieces of MIA PaCa-2 tumor harvested from similar nu/nu mice that had previously been implanted with the MIA PaCa-2 tumor. Approximately 7-10 days after tumor transplantation, when the tumor weight was approximately 50-200 mg, the mice were assigned to treatment groups such that each treatment group had a similar average tumor weight at the start of treatment. A group of mice was treated with compounds 2A, 3A, and 5A, in all cases as the hydrochloride salts dissolved in aqueous 5% dextrose, at 100 mg/Kg by intraperitoneal injection once/day for 7 consecutive days, with vehicle control. All compounds were active in this assay, with tumor growth inhibition compared to vehicle of 89%, 89%, and 62% for compounds 2A, 3A, and 5A, respectively; though all animals showed some body weight loss.

All compounds tested were safe and non-toxic at the doses tested.

Formulation and Therapeutic Examples

Formulation Example 1

Pharmaceutical Composition for Oral Administration

A solid pharmaceutical composition for oral administration is prepared by combining the following:

| | |
|---|---|
| Compound of this invention | 25.0% w/w |
| Magnesium stearate | 0.5% w/w |
| Starch | 2.0% w/w |
| Hydroxypropylmethylcellulose | 1.0% w/w |
| Microcrystalline cellulose | 71.5% w/w | and the mixture is compressed to form tablets or filled into hard gelatin capsules containing, for example, 100 mg of the compound of this invention. Tablets may be coated, if desired, by applying a suspension of a film-forming agent (for example, hydroxypropylmethylcellulose), pigment (for example, titanium dioxide), and plasticizer (for example, diethyl phthalate), and drying the film by evaporation of the solvent.

Formulation Example 2

Pharmaceutical Composition for IV Administration

A pharmaceutical composition for IV administration is prepared by dissolving a compound of this invention, for example as a pharmaceutically acceptable salt, to a concentration of 1% w/v in phosphate-buffered saline; and the solution is sterilized, for example by sterile filtration, and sealed in sterile containers containing, for example, 100 mg of a compound of this invention.

Alternatively, a lyophilized composition is prepared by dissolving a compound of this invention, again for example as a pharmaceutically acceptable salt, in a suitable buffer, for example the phosphate buffer of the phosphate-buffered saline mentioned above, sterilizing the solution and dispensing it into suitable sterile vials, lyophilizing the solution to remove the water, and sealing the vials. The lyophilized composition is reconstituted by the addition of sterile water, and the reconstituted solution may be further diluted for administration with a solution such as 0.9% sodium chloride intravenous infusion or 5% dextrose intravenous infusion.

Therapeutic Example

Therapy with Compounds of this Invention

A compound of this invention, diluted in 5% dextrose intravenous infusion, is administered intravenously over 30 minutes to a patient suffering from metastatic ovarian carcinoma at an initial dose of 100 mg/m$^2$; and this dose is increased to 250 mg/m$^2$, 500 mg/m$^2$, 750 mg/m$^2$, and 1000 mg/m$^2$. The compound is administered at 1-week intervals. The same dose escalation is administered at 2- and 3-week intervals to other patients suffering from the same cancer.

While this invention has been described in conjunction with specific embodiments and examples, it will be apparent to a person of ordinary skill in the art, having regard to that skill and this disclosure, that equivalents of the specifically disclosed materials and methods will also be applicable to this invention; and such equivalents are intended to be included within the following claims.

We claim:

1. A compound of formula A:

or its acid addition salt,
where each R is independently methyl, ethyl, propyl, or isopropyl, or —NR$_2$ together is pyrrolidin-1-yl or piperidin-1-yl.

2. The compound of claim 1 in solid form.

3. The compound of claim 1 where each R is independently methyl, ethyl, or isopropyl.

4. The compound of claim 3 where each R is the same.

5. The compound of claim 4 that is 2-{[2-(dimethylamino)ethyl]sulfonyl}ethyl N,N,N',N'-tetrakis(2-chloroethyl)phosphorodiamidate or its acid addition salt.

6. The compound of claim 4 that is 2-{[2-(diethylamino)ethyl]sulfonyl}ethyl N,N,N',N'-tetrakis(2-chloroethyl)phosphorodiamidate or its acid addition salt.

7. The compound of claim 4 that is 2-{[2-(diisopropylamino)ethyl]sulfonyl}ethyl N,N,N',N'-tetrakis(2-chloroethyl)phosphorodiamidate or its acid addition salt.

8. The compound of claim 1 that is an acid addition salt of the compound of formula A.

9. The compound of claim 8 in solid form.

10. A pharmaceutical composition comprising a compound of claim 1 and an excipient.

11. A method of preparing a compound of formula A:

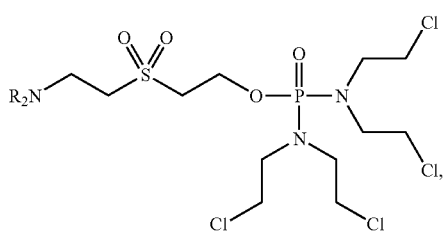

or its acid addition salt, where each R is independently methyl, ethyl, propyl, or isopropyl, or —NR$_2$ together is pyrrolidin-1-yl or piperidin-1-yl; comprising:

(a) oxidizing a corresponding compound of formula B:

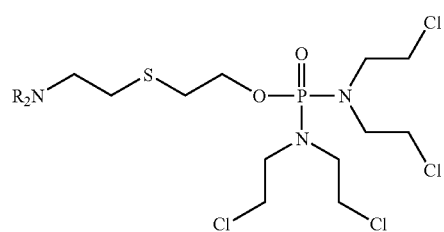

to the compound of formula A, optionally followed by one or more of:

(e) forming an acid addition salt of a compound of formula A;

(f) converting an acid addition salt of a compound of formula A to another acid addition salt of formula A; and (g) converting an acid addition salt of a compound of formula A to the non-salt form of the compound of formula A.

12. The compound of claim 6 that is an acid addition salt of 2-{[2-(diethylamino)ethyl]sulfonyl}ethyl N,N,N',N'-tetrakis(2-chloroethyl)phosphorodiamidate.

13. The compound of claim 12 in solid form.

14. The compound of claim 12 that is the citric acid addition salt of 2-{[2-(diethylamino)ethyl]sulfonyl}ethyl N,N,N',N'-tetrakis(2-chloroethyl)phosphorodiamidate.

15. The compound of claim 14 in solid form.

16. A pharmaceutical composition comprising the compound of claim 6 and an excipient.

17. A pharmaceutical composition comprising the compound of claim 12 and an excipient.

18. A pharmaceutical composition comprising the compound of claim 14 and an excipient.

* * * * *